(12) United States Patent
Rogers et al.

(10) Patent No.: US 7,488,312 B2
(45) Date of Patent: Feb. 10, 2009

(54) POLYP SCREEN

(76) Inventors: Joann E. Rogers, 966 Pine Walk Ct., NE., Palm Bay, FL (US) 32905; Marcia Caldwell, P.O. Box 627, Melbourne, FL (US) 32902

( * ) Notice: Subject to any disclaimer, the term of this patent is extended or adjusted under 35 U.S.C. 154(b) by 500 days.

(21) Appl. No.: 11/265,678

(22) Filed: Nov. 2, 2005

(65) Prior Publication Data

US 2006/0189950 A1 Aug. 24, 2006

Related U.S. Application Data

(60) Provisional application No. 60/655,565, filed on Feb. 23, 2005.

(51) Int. Cl.
*A61M 1/00* (2006.01)
*A61B 5/00* (2006.01)
*A61B 19/00* (2006.01)

(52) U.S. Cl. .................. 604/406; 600/573; 604/319

(58) Field of Classification Search .......... 604/317, 604/319, 406; 600/573, 575, 576, 578, 579, 600/580; 210/85, 232, 323.1, 443, 454, 455

See application file for complete search history.

(56) References Cited

U.S. PATENT DOCUMENTS

| 3,855,997 | A | * | 12/1974 | Sauer | .................. 600/573 |
|---|---|---|---|---|---|
| 4,250,892 | A | | 2/1981 | Dolhay et al. | |
| 4,257,425 | A | | 3/1981 | Ryan | |
| 4,643,197 | A | * | 2/1987 | Greene et al. | ............... 600/575 |
| 4,915,691 | A | | 4/1990 | Jones et al. | |
| 5,062,835 | A | | 11/1991 | Maitz et al. | |
| 5,575,293 | A | | 11/1996 | Miller et al. | |
| 5,624,418 | A | * | 4/1997 | Shepard | ..................... 604/319 |
| 6,572,578 | B1 | | 6/2003 | Blanchard | |
| 6,589,219 | B1 | * | 7/2003 | Shibuya | ..................... 604/319 |
| 6,679,835 | B2 | | 1/2004 | Moriyama | |
| 6,695,791 | B2 | | 2/2004 | Gonzalez | |
| 7,244,236 | B2 | * | 7/2007 | Merkle | ..................... 600/575 |
| 2001/0037096 | A1 | * | 11/2001 | Anderson et al. | ........... 604/322 |

* cited by examiner

*Primary Examiner*—Tatyana Zalukaeva
*Assistant Examiner*—Michael G Bogart
(74) *Attorney, Agent, or Firm*—James Ray & Associates

(57) ABSTRACT

A screen for use with a fluid/specimen collector and a combination screen and fluid/specimen collector for collecting and trapping patient specimen(s) during a medical procedure comprising a collecting trap for receiving fluid/specimen(s) therein, a lid, an intake member for transferring fluid/specimen(s) from a patient into the collecting trap, and a waste exit member. The screen of the invention comprises an insert member capable of being placed within the lid of the fluid/specimen collector. The insert member includes an intake aperture, enabling the intake member to extend through to transfer fluid/specimen(s) from a patient into the collecting trap. The insert also includes a plurality of straining apertures capable of allowing excess fluid to pass through and exit the collector through the waste exit member while preventing specimens from passing through the straining apertures, thus trapping these specimens within the collector for easy retrieval for subsequent medical testing.

20 Claims, 5 Drawing Sheets

POLYP SCREEN

CROSS-REFERENCE TO RELATED APPLICATION

This application is related to and claims priority from U.S. Provisional Patent Application titled POLYP SCREEN filed on Feb. 23, 2005 and having Ser. No. 60/655,565.

FIELD OF THE INVENTION

The present invention relates, in general, to the field of specimen collectors for the collection of patient specimen(s) for medical testing, and more particularly, to a screen for use with a specimen collector to prevent patient specimen(s) from exiting the collector device so that the patient specimen(s) may be readily retrieved for medical testing.

BACKGROUND OF THE INVENTION

Fluid/specimen collecting devices for collecting patient specimens, such as polyps, for medical testing are well known. One example of a known type of fluid/specimen collecting device is shown in FIG. 2 of the present invention. This device, generally indicated as 10, comprises a collecting trap 12 for receiving fluid/specimen(s) from a patient. A lid 14 is provided which cooperates with the collecting trap. An intake member or tube 16 is provided for transferring fluid/specimen(s) from the patient into the collecting trap. Excess fluid is then removed from the collecting trap by a well-known means, such as by the application of a vacuum thereto. The excess fluid exits through a waste exit member or tube 18 into a waste container. The patient specimen(s) is then, hopefully, trapped within the collecting trap 12, and can be removed after the procedure has been completed.

These currently used fluid/specimen collectors do not have any screening over the exit point of the waste exit member. Consequently, the specimen(s) may be inadvertently suctioned out of the collector and deposited within the waste container. When this occurs, the specimen(s) have to be searched for within the waste container and are possibly lost.

There is a need in the art for a device to prevent this unwanted removal of the patient specimen(s) from the fluid/specimen collector.

OBJECTS OF THE INVENTION

It is therefore an object of the invention to provide a screen for the prevention of unwanted removal of patient specimen(s) or polyps from within fluid/specimen collecting devices.

It is yet another object of the invention to provide a screen which may be used with fluid/specimen collecting devices that are currently on the market.

It is still yet another object of the invention to provide a screen for use with fluid/specimen collecting devices which is cost effective.

It is still yet another object of the invention to provide a screen for use with fluid/specimen collecting devices which is easy to position within the collecting device.

It is a further object of the invention to provide a screen for use with fluid/specimen collecting devices which may be readily removed from the collector.

It is still a further object of the invention to provide a screen for use with fluid/specimen collecting devices which is disposable.

In addition to the various objects and advantages of the invention which have been described in some specific detail above it should be noted that various other objects and advantages of the present invention will become more readily apparent to those persons who are skilled in the relevant art from the following more detailed description, particularly, when such description is taken in conjunction with the attached drawing Figures and with the appended claims.

SUMMARY OF THE INVENTION

Briefly, and in accordance with the forgoing objects, the invention comprises a screen for use with a fluid/specimen collector for collecting and trapping patient specimen(s) during a medical procedure, wherein the fluid/specimen collector comprises a collecting trap for receiving fluid/specimen(s) therein, a lid cooperating with the collecting trap, an intake member for transferring fluid/specimen(s) from a patient into the collecting trap, and a waste exit member for transferring excess fluid from the collecting trap into a waste container. The screen of the invention comprises an insert member capable of being placed within the lid of the fluid/specimen collector. The insert member includes an intake aperture extending there through which has a predetermined size and shape to enable the intake member to extend through to transfer fluid/specimen(s) from a patient into the collecting trap. The insert also includes a plurality of straining apertures extending there through. These straining apertures have a predetermined size and shape capable of allowing excess fluid to pass through and exit the collector through the waste exit member while preventing specimens from passing through the straining apertures and trapping these specimens within the fluid/specimen collector for easy retrieval for subsequent medical testing.

DETAILED DESCRIPTION OF THE INVENTION

Figure 1:
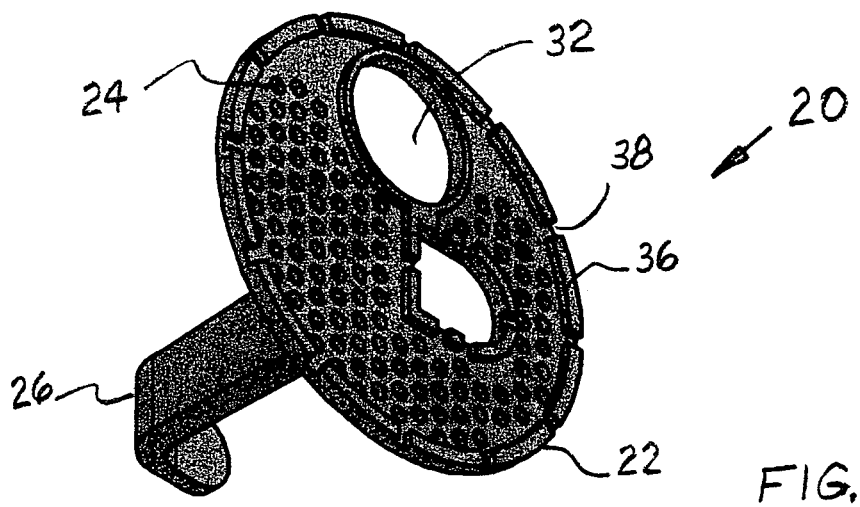
FIG. 1 shows a perspective view of the specimen/polyp screen of the invention.
Figure 3:
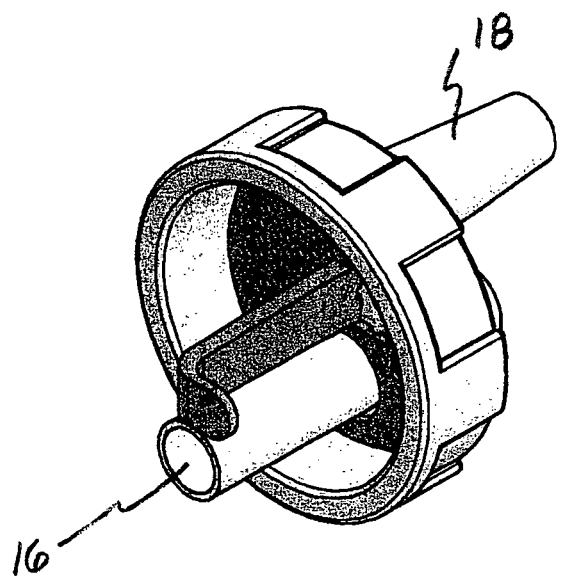
FIG. 3 shows a perspective view of the specimen/polyp screen of the invention position within a lid of a fluid/specimen collector.
Figure 4:
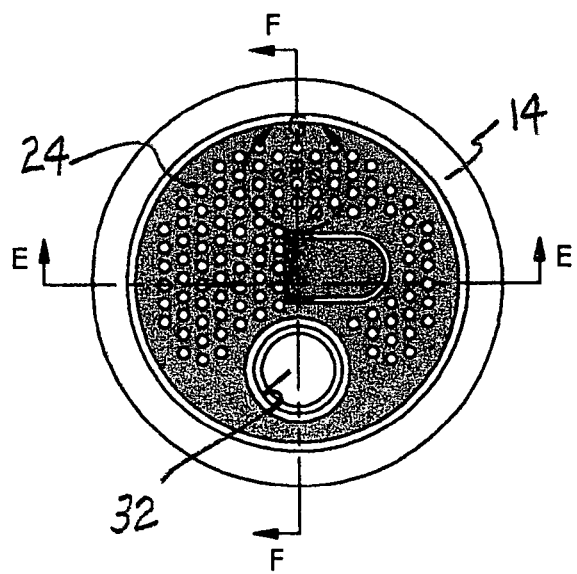
FIG. 4 shows a front view of the specimen/polyp screen of the invention positioned within a lid of a fluid/specimen collector.

Before describing the invention in detail, the reader is advised that, for the sake of clarity and understanding, identical components having identical functions have been marked where possible with the same reference numerals in each of the Figures provided in this document.

Figure 2:
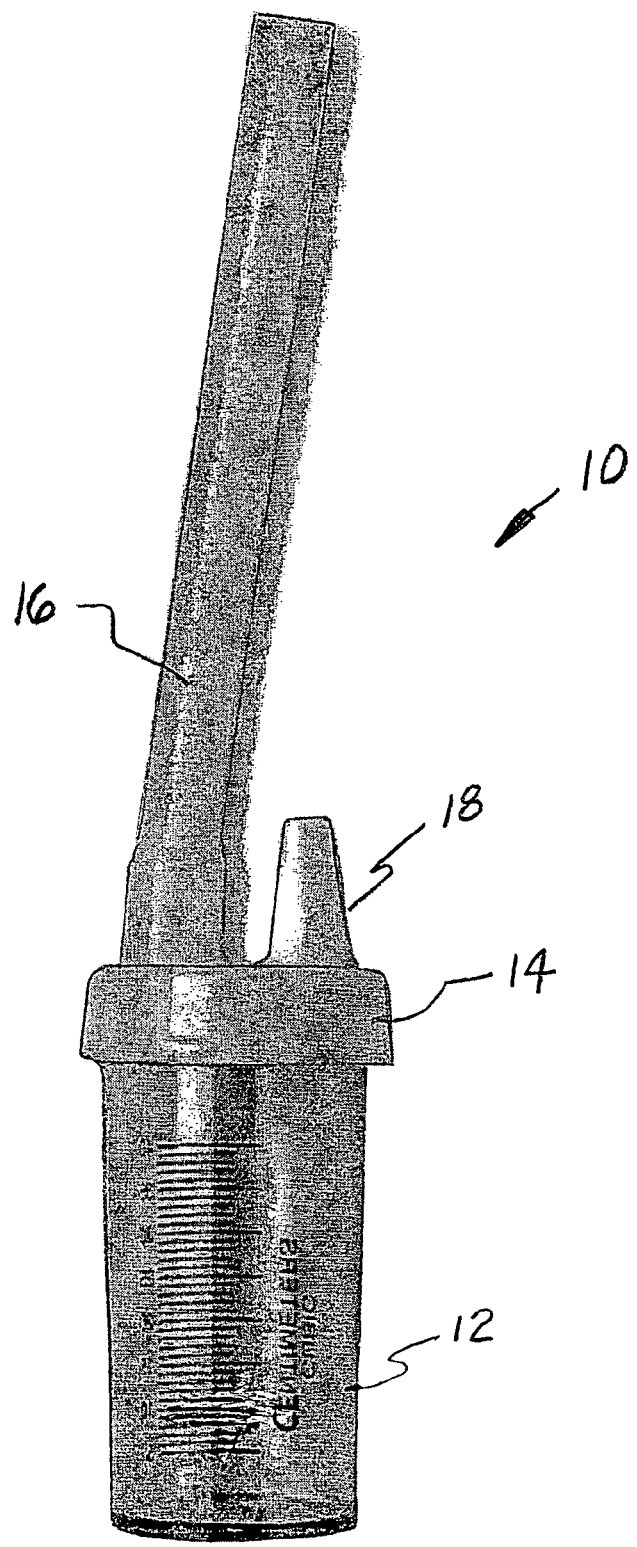
FIG. 2 shows an example of a prior art fluid/specimen collector with which the specimen/polyp screen of the invention can be used.
Figure 5:
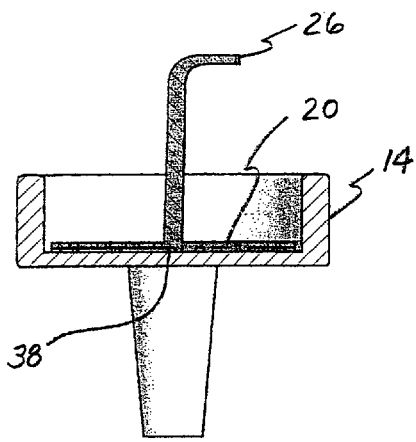
FIG. 5 shows the specimen/polyp screen of the invention positioned within a lid of a fluid/specimen collector taken along line E-E of FIG. 4.
Figure 6:
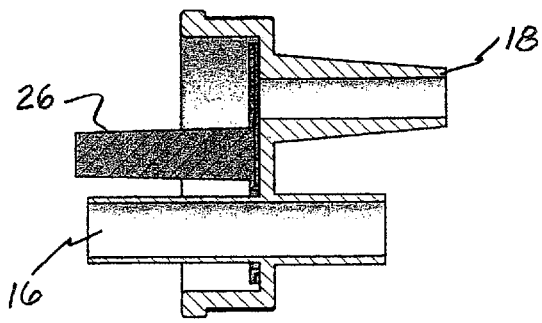
FIG. 6 shows the specimen/polyp screen of the invention positioned within a lid of a fluid/specimen collector taken along line F-F of FIG. 4.
Figure 7:
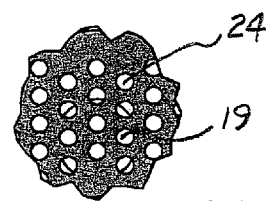
FIG. 7 shows a partial view of a portion of the specimen/polyp screen of the invention positioned over the waste exit member a fluid/specimen collector.
Figure 8A:
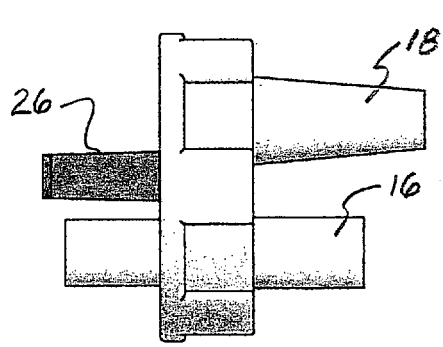
FIGS. 8A and 8B show side views of the specimen/polyp screen of the invention positioned within a lid of a fluid/specimen collector taken along portion G of FIG. 4.
Figure 8B:
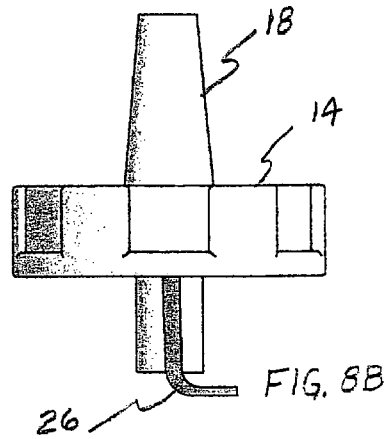

Now reference is made to FIG. 1 which shows a screen, generally indicated 20, for use with a fluid/specimen collector. The fluid/specimen collector can be any type of well-known collector, an example of which is generally indicated as 10 in FIG. 2. The fluid/specimen collector 10 comprises a collecting trap 12 for receiving fluid/specimen(s) therein, a lid 14 which is capable of attachment to the collecting trap 12 by any well known means such as by screw fit, snap fit, and the like. An intake member, such as a tube 16 is provided for transferring fluid/specimen(s) from a patient into the collecting trap 12. A waste exit member, which may be a tube 18 attached to an opening 19, as shown in FIG. 7, in the lid 14 is provided for transferring excess fluid from the collecting trap 12 into a waste container (not shown). This excess fluid is typically removed by means of a vacuum.

The screen 20 of the invention comprises an insert member 22 capable of being placed within the lid 14 of the fluid/specimen collector 10. A plurality of straining apertures 24 are provided which extend through the insert member 22. The straining apertures 24 have a predetermined size and shape which is large enough to allow excess fluid to pass there through and exit the collector 10 via the waste exit member 18, but which is small enough to prevent patient specimen(s) from exiting through the waste exit member 18, 19. Consequently, the specimen(s) are trapped within the fluid/specimen collector 10 and can be easily retrieved for medical testing.

Figure 9:
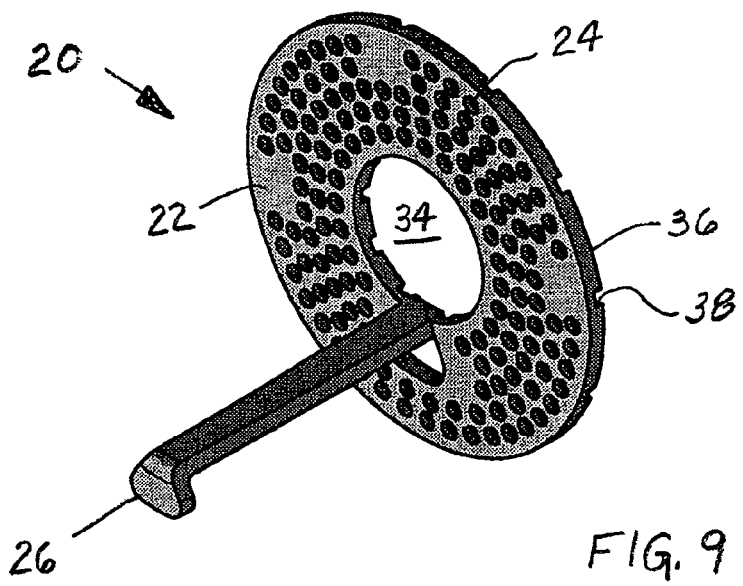
FIG. 9 shows a perspective view of the specimen/polyp screen according to a second embodiment of the invention.
Figure 10:
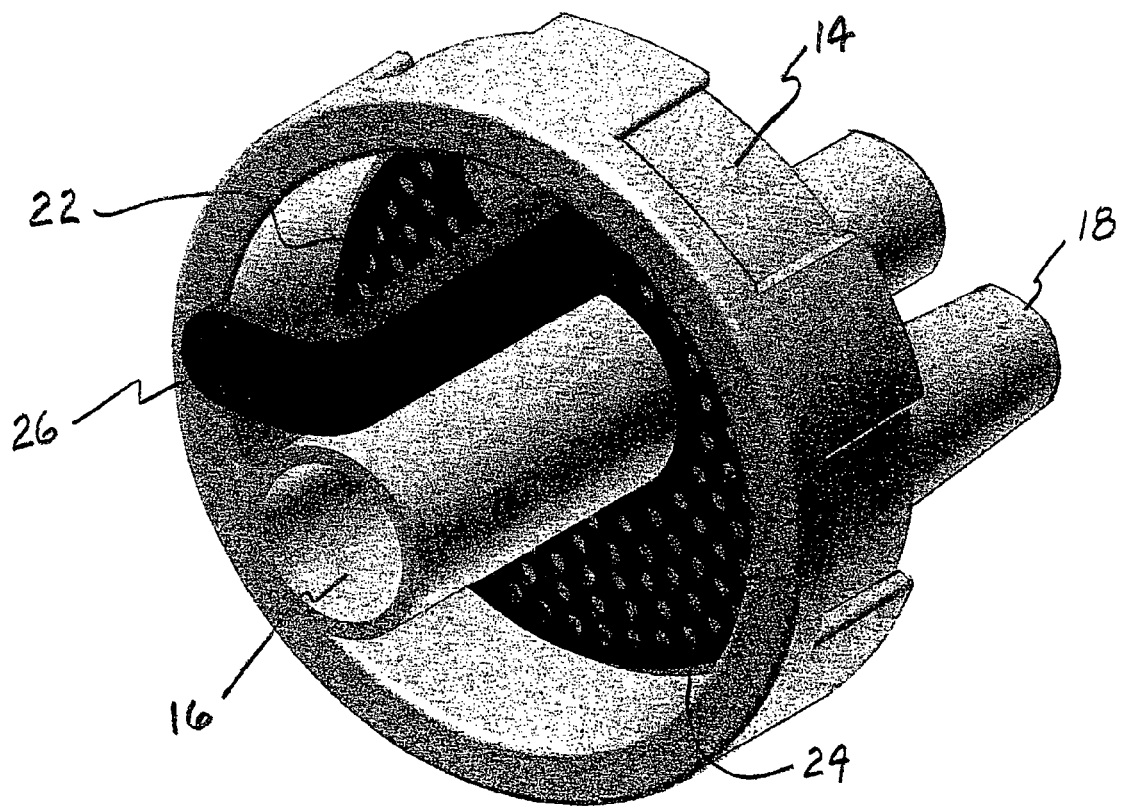
FIG. 10 shows a perspective view of the specimen/polyp screen of FIG. 9 positioned within a lid of a fluid/specimen collector.
Figure 11A:
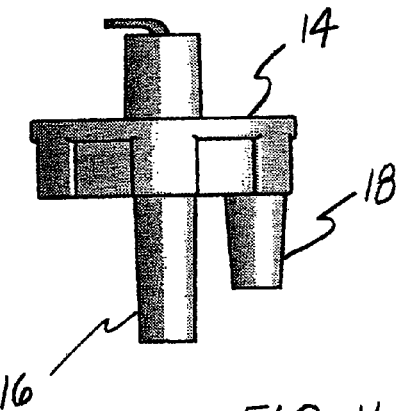
FIGS. 11A and 11B show side views of the FIG. 9 embodiment of the specimen/polyp screen positioned within a lid of a fluid/specimen collector.
Figure 11B:
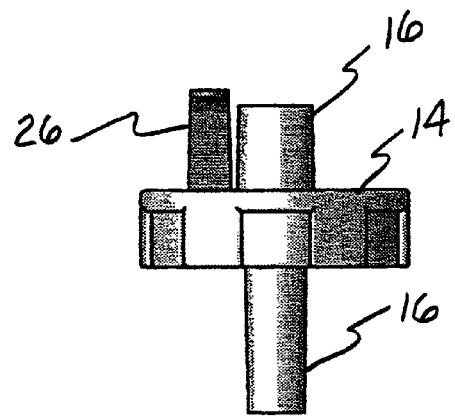

As shown in FIGS. 1 and 3-6 and 9, the insert member 22 is a disc shaped member and includes an intake aperture having a predetermined size and shape capable of allowing the intake member 16 to extend there through to transfer fluid/specimen(s) from the patient into the collecting trap 12. FIG. 1 shows the specimen/polyp screen according to a first embodiment wherein the insert member 22 includes an intake aperture 32 positioned to the side of the insert member. FIG. 9 shows the specimen/polyp screen according to a second embodiment wherein the insert member 22 includes an intake aperture 34 positioned in the center of the insert member 22.

Figure 13:
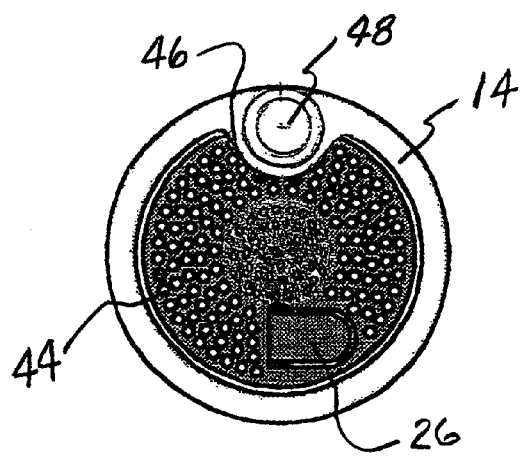
FIG. 13 shows a front view of the specimen/polyp screen positioned within a lid of the fluid/specimen collector according to a fourth embodiment.

In an alternative embodiment, as illustrated in FIG. 13, the insert member 44 can be formed in a crescent shape and the intake aperture 48 of the insert member 44 includes a cut-out portion 46 having a predetermined size and shape capable of accommodating the intake member 16 and allowing the intake member 16 to extend into the collecting trap 12 to transfer fluid/specimen(s) from a patient into the collecting trap 12.

As illustrated in FIGS. 1, 3, 5-6 and 9, a means is provided for removing the screen 20 from the lid 14. This means may a handle 26 extending outward from the insert member 12. Preferably the handle 26 and insert member 22 are an integrally molded single piece, however any well known means may be provided for attaching the handle 26 to the insert member 22.

The insert member 22 may be held in place within the lid 14 by any well-known means. Preferably, the insert member 22 is held in place simply by means of attachment of the lid 14 to the collecting trap 12. Alternatively, the insert member 22 may be held within the lid 14 by a snap-fit of the edges of the insert member 22 within an inner edge portion of the lid 14.

As shown in FIGS. 1, 5-6 and 9, the insert member 22 includes feet 36 which are positioned adjacent the lid 14 so as to produce at least one air gap 38 between the insert member 22 and the lid 14.

The screen 20 can be formed from any well known material including plastic, metal, composite, and the like. Preferably, the screen 20 is formed from a plastic material wherein the insert member 22 is a single molded piece. The apertures 24 are then formed through this single molded piece.

Figure 12:
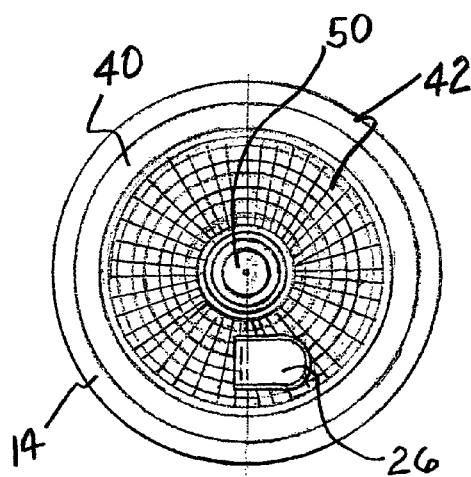
FIG. 12 shows a front view of a specimen/polyp screen positioned within a lid of a fluid/specimen collector according to a third embodiment.

Alternatively, as shown in FIG. 12, the screen 20 can be formed from an insert member 22 comprising a frame 40 surrounding a screen mesh member 42, both of which are formed from well known materials. The handle 26 can be attached to the screen mesh member 42 or alternatively be attached to the frame 40. The screen mesh member 42 includes an aperture 50 through which intake member 16 extends.

The invention has been described in such full, clear, concise, and exact terms so as to enable any person skilled in the art to which it pertains to make and use the same. It should be understood that variations, modifications, equivalents and substitutions for components of the specifically described embodiments of the invention may be made by those skilled in the art without departing from the spirit and scope of the invention as set forth in the appended claims. Persons who possess such skill will also recognize that the foregoing description is merely illustrative and not intended to limit any of the ensuing claims to any particular narrow interpretation.

We claim:

1. A screen for use with a fluid/specimen collector for collecting and trapping patient specimen(s) during a medical procedure, such fluid/specimen collector including a collecting trap for receiving fluid/specimen(s) therein, a lid cooperating with such collecting trap, an intake member for transferring fluid/specimen(s) from a patient into such collecting trap, and a waste exit member for transferring excess fluid from such collecting trap into a waste container, said screen comprising:

(a) an insert member capable of being placed within such lid of such fluid/specimen collector, said insert member having feet which are positioned adjacent such lid, said feet having a predetermined size and shape capable of producing at least one air gap between said insert member and such lid;

(b) an intake aperture extending through said insert member, said intake aperture having a predetermined size and shape to enable such intake member to extend through said insert member and to transfer fluid/specimen(s) from a patient into such collecting trap, and (c) a plurality of straining apertures extending through said insert member, said straining apertures having a predetermined size and shape capable of allowing excess fluid -to pass there through and exit such collector through such waste exit member while preventing specimens from passing through said straining apertures and trapping such specimens within such fluid/specimen collector.

2. A screen for use with a fluid/specimen collector as recited in claim 1 further including a means for removing said screen from within such lid.

3. A screen for use with a fluid/specimen collector as recited in claim 2 wherein said means for removing said screen comprises a handle extending outward from said insert member.

4. A screen for use with a fluid/specimen collector as recited in claim 3 wherein said handle and insert member are an integrally molded single piece.

5. A screen for use with a fluid/specimen collector as recited in claim 1 wherein said insert member is placed within such lid and held in place by means of attachment of such lid to such collecting trap.

6. A screen for use with a fluid/specimen collector as recited in claim 1 wherein said insert member is a single molded piece and said intake aperture and straining apertures are formed through said single molded piece.

7. A screen for use with a fluid/specimen collector as recited in claim 1 wherein said insert member comprises a frame surrounding a screen mesh member and said intake aperture extends through said screen mesh member.

8. A screen for use with a fluid/specimen collector as recited in claim 7 further including a handle positioned on one of said frame and said screen mesh member for removing said screen from within such lid.

9. A screen for use with a fluid/specimen collector as recited in claim 1 wherein said insert member is crescent shaped and said intake aperture includes a cutout portion having a predetermined size and shape capable of accommodating such intake member and allowing such intake member to extend into such collecting trap to transfer fluid/specimen(s) from a patient into such collecting trap.

10. A screen for use with a fluid/specimen collector as recited in claim 9 including a handle integrally molded with said insert member for removing said screen from within such lid.

11. A fluid/specimen collector and screen combination for collecting and trapping patient specimen(s) during a medical procedure, said fluid/specimen collector and screen combination comprising:
(a) a collecting trap for receiving fluid/specimen (s) therein;
(b) a lid cooperating with said collecting trap; (c) an intake member for transferring fluid/specimen(s) from a patient into said collecting trap;
(d) a waste exit member for transferring excess fluid from said collecting trap into a waste container;
(e) a screen capable of being placed within said lid, said screen including an insert member formed as a frame surrounding a screen mesh member having an intake aperture extending there through and having an intake member extending there through having a predetermined size and shape capable of allowing said intake member to extend there through for transferring fluid/specimen(s) from a patient into said collecting trap, said screen further including a plurality of straining apertures extending through said insert member, said apertures having a predetermined size and shape capable of allowing excess fluid to pass there through and exit said collector through said waste exit member while preventing specimen(s) from passing through said apertures and trapping such specimens within said fluid/specimen collector.

12. A screen for use with a fluid/specimen collector as recited in claim 11 further including a means for removing said screen from within said lid.

13. A screen for use with a fluid/specimen collector as recited in claim 12 wherein said means for removing said screen comprises a handle extending outward from said insert member.

14. A screen for use with a fluid/specimen collector as recited in claim 13 wherein said handle and insert member are an integrally molded single piece.

15. A screen for use with a fluid/specimen collector as recited in claim 11 wherein said insert member is placed within said lid and held in place by means of attachment of said lid to said collecting trap.

16. A screen for use with a fluid/specimen collector as recited in claim 11 wherein said insert member includes feet which are positioned adjacent said lid, said feet having a predetermined size and shape capable of producing at least one air gap between said insert member and said lid.

17. A screen for use with a fluid/specimen collector as recited in claim 11 wherein said insert member comprises a frame surrounding a screen mesh member and said intake aperture extends through said screen mesh member.

18. A screen for use with a fluid/specimen collector as recited in claim 17 further including a handle positioned on one of said frame and said screen mesh member for removing said screen from within said lid.

19. A screen for use with a fluid/specimen collector as recited in claim 11 wherein said insert member is crescent shaped and said intake aperture includes a cut-out portion having a predetermined size and shape capable of accommodating said intake member and allowing said intake member to extend into said collecting trap to transfer fluid/specimen(s) from a patient into said collecting trap.

20. A screen for use with a fluid/specimen collector as recited in claim 19 including a handle integrally molded with said insert member for removing said screen from within said lid.

* * * * *